(12) United States Patent
Frochaux et al.

(10) Patent No.: US 9,474,494 B2
(45) Date of Patent: Oct. 25, 2016

(54) INTERFACE DEVICE BETWEEN A USER AND A SURGICAL OR DENTAL INSTRUMENT

(75) Inventors: Damien Frochaux, Colombier (CH); Marco Gallina, Ins (CH)

(73) Assignee: Bien-Air Holding SA, Bienne (CH)

( * ) Notice: Subject to any disclaimer, the term of this patent is extended or adjusted under 35 U.S.C. 154(b) by 515 days.

(21) Appl. No.: 13/697,290

(22) PCT Filed: May 10, 2011

(86) PCT No.: PCT/EP2011/057461
§ 371 (c)(1),
(2), (4) Date: Jan. 10, 2013

(87) PCT Pub. No.: WO2011/141442
PCT Pub. Date: Nov. 17, 2011

(65) Prior Publication Data
US 2013/0116805 A1     May 9, 2013

(30) Foreign Application Priority Data

May 12, 2010   (EP) ..................................... 10162731

(51) Int. Cl.
*A61B 6/14* (2006.01)
*A61C 1/00* (2006.01)
*A61C 19/00* (2006.01)
(Continued)

(52) U.S. Cl.
CPC ............... *A61B 6/14* (2013.01); *A61C 1/0015* (2013.01); *A61C 19/00* (2013.01); *G05B 15/02* (2013.01); *A61B 2017/00199* (2013.01); *A61G 2203/12* (2013.01); *A61G 2203/20* (2013.01)

(58) Field of Classification Search
CPC .................. A61B 19/2203; A61B 217/00199; A61B 2017/00734; A61B 2019/2223; A61B 6/14; A61G 15/00; A61G 2203/12; A61G 2203/20; G06F 1/1626; G06F 1/1632; G06F 1/1635; G06F 1/1698; G06F 19/3406; G06F 19/3412; G06F 19/3418; A61C 19/00; H04W 88/00
USPC ............... 700/11, 17, 19, 56, 60, 65, 66, 83; 705/2
See application file for complete search history.

(56) References Cited

U.S. PATENT DOCUMENTS 5,989,247 A * 11/1999 Chambers ....................... 606/41
6,405,049 B2 * 6/2002 Herrod et al. ................. 455/517

(Continued)

FOREIGN PATENT DOCUMENTS

WO     2004/084753 A1     10/2004
WO     2007/060292 A1     5/2007

OTHER PUBLICATIONS

International Search Report issued in corresponding application PCT/EP2011/057461, completed Jul. 8, 2011 and mailed Jul. 15, 2011.

*Primary Examiner* — Crystal J Barnes-Bullock
(74) *Attorney, Agent, or Firm* — Oblon, McClelland, Maier & Neustadt, L.L.P.

(57) ABSTRACT

Portable human-machine interface device intended to be removably connected to a controller (2) of at least one surgical or dental instrument (4), the controller (2) being installed in a power and control unit (6) or a table top equipment (8), the interface device (1) including hardware and software means allowing a user to enter an instruction or data into the interface device (1) to control, via the controller (2), the operation of the surgical or dental instrument (4).

17 Claims, 2 Drawing Sheets

(51) Int. Cl.
  *G05B 15/02* (2006.01)
  *A61B 17/00* (2006.01)

(56) References Cited

U.S. PATENT DOCUMENTS

| | | | | |
|---|---|---|---|---|
| 6,560,492 | B2* | 5/2003 | Borders | 700/17 |
| 6,981,941 | B2* | 1/2006 | Whitman et al. | 600/1 |
| 8,620,462 | B2* | 12/2013 | Nyholm | 700/83 |
| 2002/0128661 | A1* | 9/2002 | Brock et al. | 606/130 |
| 2006/0127840 | A1* | 6/2006 | Fornoff et al. | 433/77 |
| 2007/0149881 | A1* | 6/2007 | Rabin | 600/471 |
| 2007/0208999 | A1* | 9/2007 | Gmeinder | H04N 7/18 715/700 |
| 2007/0239289 | A1* | 10/2007 | Cambre et al. | 700/64 |
| 2008/0281301 | A1* | 11/2008 | DeBoer | G06F 19/3487 606/1 |
| 2009/0090763 | A1 | 4/2009 | Zemlok et al. | |
| 2010/0063508 | A1* | 3/2010 | Borja et al. | 606/88 |
| 2013/0297330 | A1* | 11/2013 | Kamen et al. | 705/2 |
| 2014/0002364 | A1* | 1/2014 | Ibsies | 345/168 |

* cited by examiner

INTERFACE DEVICE BETWEEN A USER AND A SURGICAL OR DENTAL INSTRUMENT

This is a National Phase Application in the United States of International Patent Application PCT/EP 2011/057461 filed May 10, 2011, which claims priority on European Patent Application No. 10162731.3. The entire disclosures of the above patent applications are hereby incorporated by reference.

FIELD OF THE INVENTION

The present invention concerns an interface device between a user and a surgical or dental instrument. More specifically, the invention concerns a removable and versatile interface device.

BACKGROUND OF THE INVENTION

The dental surgery environment has considerably changed in the last few years. In order to provide patients with increasingly complete services in comforting and modern surroundings, practitioners invest in more and more sophisticated equipment. Moreover, faced with the endlessly increasing diversity of clinical treatments (restoration, endodontics, prophylaxis, orthodontics, implants, etc.) offered by practitioners, the necessary number of instruments has considerably increased.

However, the work space of the practitioner is limited. All the instruments necessary for the treatment must be grouped around the patient seated in the chair and they must remain within the practitioner's reach. Further, the instruments must be able to be changed quickly during treatment and between two successive patients. Likewise, the instruments must be able to be used simply and in conditions of impeccable hygiene to reduce as far as possible any risk of error in handling or of contamination.

To satisfy these new requirements, each medical equipment manufacturer provides its own response attempting to distinguish itself from the competitors. To achieve this, manufacturers create work environments which differ from those of competitors as regards both hardware and software. Manufacturers will, for example, offer a user interface with a new graphical presentation, a touch screen or the possibility of choosing the language of use.

Faced with such an abundance of supply, practitioners are often unable to become sufficiently familiar with the work environment peculiar to each manufacturer to be able to use the numerous pieces of equipment available in an intuitive manner, which may lead to risks both for practitioners and their patients.

To overcome these problems, the tendency seen for several years has been to group together the largest possible number of instruments within the same power and control unit (commonly called a "unit") so that the user interface of the unit can be used to control all of the instruments. However, the control means of the unit does not always have the flexibility necessary for all the functions of the instruments to be used. Moreover, practitioners often wish to fit additional instruments to their unit sometimes long after the unit has been purchased. In this case too, the facility of use and versatility of the user interface fitted to the unit are key factors in the successful and risk-free integration of new instruments in the unit.

In some cases, however, it is not possible to modernise the unit and the practitioner has to purchase table top equipment in addition to the instruments integrated in the dental unit. The number of user interfaces that the practitioner has to manage therefore has a tendency to increase, which may constitute a risk for the practitioner or the patient, or at least a lack of efficiency.

Further, nowadays an increasing number of dental clinics are being set up in which several practitioners work in a team and combine their area of clinical specializations in order to offer a complete service to patients. These dental clinics also allow practitioners to share both working expenses (personal assistant, rent, etc.) and investment costs.

However, although equipment is shared, each practitioner wishes to continue with the same work habits. Thus, there is a requirement for versatile work tools which can be used in an extremely flexible way by several people. The equipment, in particular dental units and table top equipment, must therefore be able to be adapted to the requirements of each user.

SUMMARY OF THE INVENTION

It is an object of the present invention to satisfy this requirement, in addition to others, by providing an interface device between a user and a surgical or dental instrument which enables a user to recreate the work environment that he is used to in the context where equipment is shared between several users The present invention therefore concerns a portable human-machine interface device intended to be removably connected to a controller of at least one surgical or dental instrument, said interface device including hardware and software means allowing a user to enter an instruction or data into the interface device to control, via the controller, the operation of the surgical or dental instrument.

Owing to these features, the present invention provides a removable human-machine interface device via which the user can recreate the work environment that he is used to simply by connecting the interface device to the controller of the surgical or dental instruments that the user wishes to employ. The portable and removable nature of the interface device according to the invention thus enables the user, wherever he is, always to have at his disposal the user programmes for each different instrument. Moreover, the removable nature of the interface device allows several users to share the same equipment, each user being provided with his own interface device allowing him to work in his usual manner.

According to a complementary feature of the invention, the interface device and the controller form a master/slave assembly in which the interface device is the master and the controller is the slave.

According to another feature of the invention, the interface device includes hardware and software means for processing the data originating from the controller of the surgical or dental instrument and sending back the corresponding instructions to the controller.

According to yet another feature of the invention, the interface device includes hardware and software means for processing and storing the data from the controller of the surgical or dental instrument and exporting this information to a resident or remote database.

According to yet another feature of the invention, the interface device includes at least one keyboard allowing the user to enter an instruction or data and at least one means of displaying data.

BRIEF DESCRIPTION OF THE DRAWINGS

Other features and advantages of the present invention will appear more clearly from the following detailed description of an embodiment of the human-machine interface device according to the invention, this example being given solely by way of non-limiting illustration with reference to the annexed drawing, in which.

DETAILED DESCRIPTION OF THE INVENTION

The present invention started from the observation that practitioners, dentists or surgeons are required to use an ever increasing number of surgical or dental instruments in the daily practice of their profession. To deal with this situation, the tendency is to fit the power and control units (commonly called a "unit") with the largest possible number of instruments so that the user interface of the unit can be used to control all the instruments. However, the control means of the unit does not always have the flexibility necessary for all the functions of the instruments to be used. This is why practitioners often have to purchase additional instruments commonly called "table top equipment". However, the combined use of the unit instruments and the table top equipment is not always problem free for the practitioner. Indeed, it is not unusual for the user environment of the unit instruments and of the table top equipment instruments to be different. Practitioners must therefore constantly juggle with different user environments or interfaces with which they are not equally familiar. This thus means an additional work load for the practitioners which represents a risk for the practitioners themselves or for their patients. Further, with the development of dental clinics which group together several practitioners, there is the problem of shared use of common equipment. It is in fact desirable for each practitioner, taking over from one of his colleagues, to find the user environment he is used to as quickly as possible. In the state of the art, this can only be achieved with numerous prior adjustments which are a waste of time and involve the risk of errors. There was therefore a need in the state of the art for a device providing a universal human-machine interface for use with a variety of instruments in an identical contextual environment, which could be transported from one piece of equipment to another.

It is therefore an object of the present invention to satisfy this requirement by providing a human-machine interface device intended to be removably connected to a controller of at least one surgical or dental instrument.

Figure 1A:
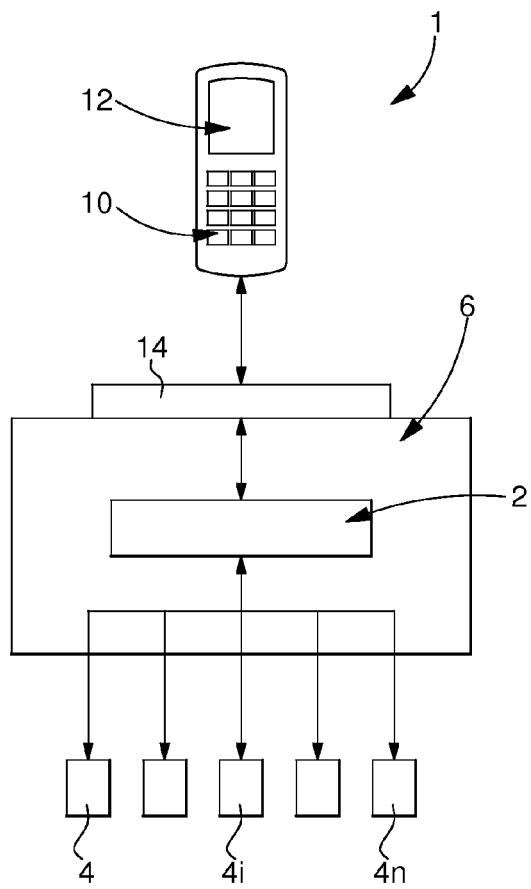
FIGS. 1A and 1B illustrate schematically the connection between an interface device according to the invention and a power and control unit or, respectively, a piece of table top equipment.

Designated as a whole by the general reference numeral 1 (see FIG. 1A), this interface device includes hardware and software means allowing a user to enter an instruction or data into the interface device 1 according to the invention to control, via a controller 2, operation of a surgical or dental instrument selected from a plurality of instruments, 4 . . . , 4i . . . , 4n.

"Controller" means a system that groups together the electronic power circuits for supplying electric current to at least one surgical or dental instrument 4 and the algorithm programmes for regulating the operation of instrument 4. By design, controller 2 is a sedentary system which is enclosed in the frame of a power and control unit (known as a "unit") 6 or a piece of table top equipment 8.

Controller 2 controls the operation of at least one surgical or dental instrument 4. "Instrument" means in a non-limiting manner one or several motors, handpieces, contra-angles, turbines, tartar removers, electric saws and other devices. These instruments may be connected to unit 6 or to table top equipment 8.

Figure 1B:
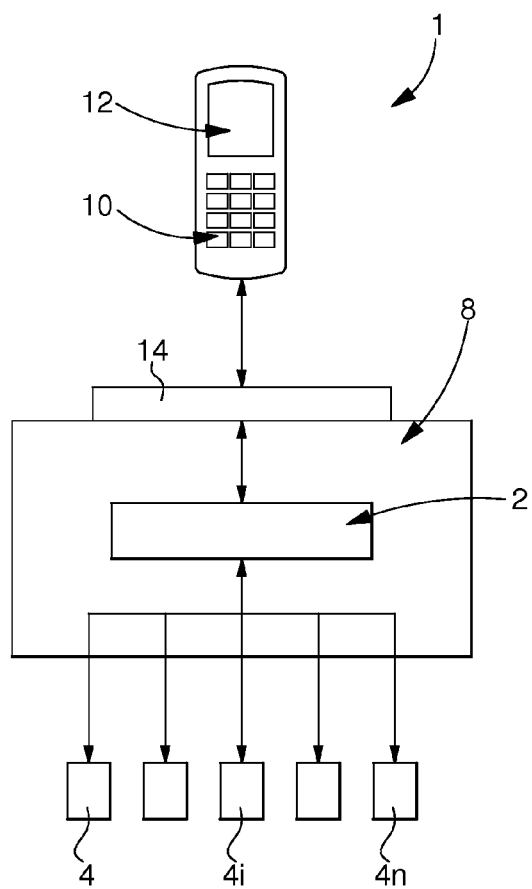
Figure 2:
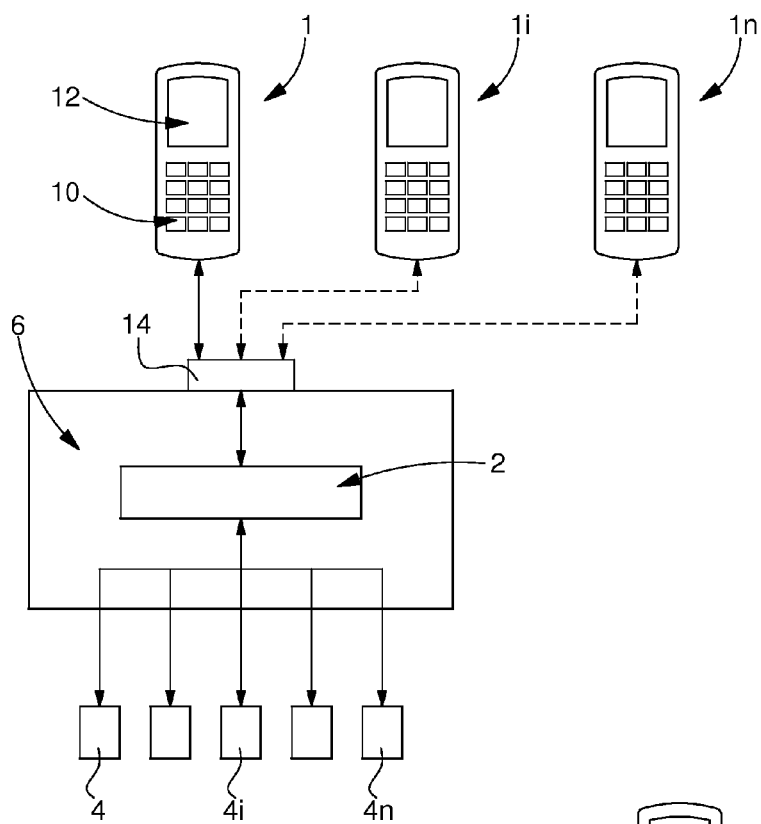
FIG. 2 schematically illustrates the connection between several interface devices according to the invention and the same power and control unit.

According to the invention, the same interface device 1, via the same controller 2, integrated for example in a unit 6, controls several surgical or dental instruments 4, . . . , 4i . . . , 4n. Moreover, the same interface device 1 may be connected to different controllers 2, integrated for example in a unit 6 and in a piece of table top equipment 8 (see FIG. 1B). Finally, several interface devices 1, . . . , 1i, . . . , 1n belonging to different users can be connected to the same controller 2 (see FIG. 2).

To enable a user to control the operation of a given surgical or dental instrument 4, interface device 1 according to the invention includes at least one keyboard 10 allowing the user to enter an instruction or data and at least one means of displaying information 12. According to a first embodiment, keyboard 10 is a real keypad combined with a display screen for example a liquid crystal display. According to a second embodiment, keyboard 10 and display device 12 are combined in a touch screen which includes a virtual keyboard and a display screen.

Figure 3:
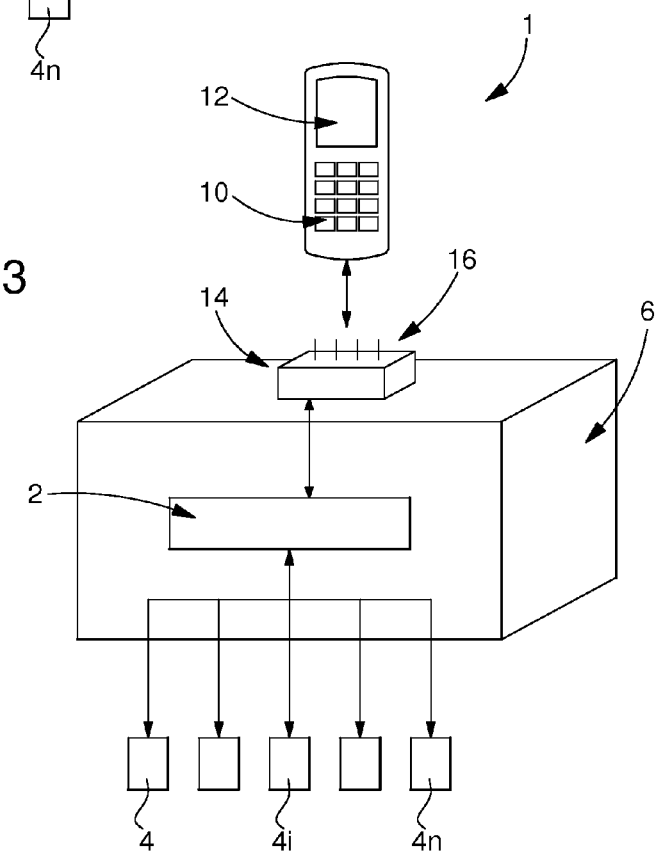
FIG. 3 schematically illustrates a power and control unit fitted with a base for receiving an interface device according to the invention.

A given interface device 1 is connected to controller 2 for example of a unit 6 via a wired connection or wireless connection. In the case of a wired connection between interface device 1 and controller 2, this connection may be achieved via a base or docket station 14 placed on or fixedly integrated in unit 6 at a place arranged for such purpose. The fact that interface device 1 is placed on its base 14 ensures the mechanical stability of interface device 1 and automatically sets up the electrical connection between interface device 1 and controller 2 of unit 6. The electrical connection may be achieved via a specific electric connector 16 (see FIG. 3).

It will be noted that depending on the type of interface device 1 and case thereof employed, the base 14 provided for receiving interface device 1 may vary, differing for example in the geometry of the place which houses interface device 1, the position of the connector or even the design (colour, shape). Any risk of improper use of interface device 1 is thus avoided.

Interface device 1 according to the invention may be a device available on the consumer market such as for example a smartphone like an i-Phone® or any other apparatus provided with a keyboard and screen as described above and able to communicate with the external environment via a wired or wireless connection.

Interface device 1 according to the invention can communicate with controller 2 of surgical or dental instrument 4 via a digital communication protocol. In the case of the present invention, an RS-232 serial communication bus was chosen, mainly for reasons of simplicity of implementation and security of use. It goes without saying however that other communication protocols such as Ethernet, USB, CAN, RS-485, any type of local bus or wireless communication protocols such as Bluetooth may also be envisaged.

Interface device 1 according to the invention may be powered via controller 2, which is in turn powered by unit 6 or table top equipment 8 in which it is implemented. According to a variant, interface device 1 may operate by means of ordinary batteries or rechargeable batteries which can be recharged by controller 2 integrated in unit 6 or even by means of a separate charger. Finally, it is possible to envisage directly connecting the interface device 1 to the electric power grid.

According to the invention, interface device 1 includes hardware and software means for processing the information supplied by the user and controller 2 and for sending instructions to controller 2 and to display device 12. Interface device 1 and controller 2 therefore form a master/slave assembly in which interface device 1 is the master and controller 2 is the slave.

The software implemented in interface device 1 therefore includes, in particular, all the programmes necessary for using surgical or dental instrument 4 connected to unit 6 or to table top equipment 8 and the communication protocol between interface device 1 and controller 2. Several user programmes each corresponding to a different instrument can be installed in interface device 1. Alternatively, the same software includes the user programmes for several instruments.

The data processing user programmes for the various instruments 4 can be loaded in interface device 1 according to the invention from a personal computer by means of an integrated connector, via a wireless connection or by means of a USB stick which is directly connected to interface device 1. It is also possible to envisage downloading programmes from an internet site. Other computer applications, for example, for storing and processing data gathered during surgical operations to form patient databases, or for managing a diary may also be installed in interface device 1.

Using the same transmission channels as those mentioned above, the data contained in an interface device 1 could also be exported to a central server or the data from two such interface devices could be synchronised.

It goes without saying that this invention is not limited to the embodiment that has just been described and that various simple alterations and variants can be envisaged by those skilled in the art without departing from the scope of the invention as defined by the claims annexed to this Patent Application. It will be noted that, for reasons of security, it is not recommended to open any applications other than those necessary for using the instruments required for the treatment.

The invention claimed is:

1. A portable human-machine interface device, comprising:
    hardware including a first circuitry, the hardware removably connected to a second controller circuitry of at least one surgical or dental instrument, the second controller circuitry being installed in a power/control unit or in a table top equipment;
    one or more software modules, executable by the first circuitry, permitting a user to enter an instruction or data to control, via the second controller circuitry, operation of the at least one surgical or dental instrument,
    wherein the one or more software modules further include
    at least one control program to control the at least one surgical or dental instrument connected to the power/control unit or to the table top equipment via the second controller circuitry,
    a communication protocol for communication between the first circuitry and the second controller circuitry, and
    a plurality of user programs, each user program corresponding to a different surgical or dental instrument, and a program to save and recreate a work environment in response to disconnection and connection of the first circuitry from/to the second controller circuitry of the at least one surgical or dental instrument.

2. The interface device according to claim 1, wherein the first circuitry and the second controller circuitry form a master/slave assembly in which the first circuitry is the master and the second controller circuitry is the slave.

3. The interface device according to claim 2, wherein the first circuitry is further configured to process the information from the second controller circuitry of the at least one surgical or dental instrument and to send back the corresponding instructions to the second controller circuitry.

4. The interface device according to claim 3,
    wherein the hardware further includes a display, and
    wherein the first circuitry is further configured to instruct display of information from the second controller circuitry of the at least one surgical or dental instrument and the instructions or data entered by the user on the display.

5. The interface device according to claim 4, wherein the first circuitry is further configured to process and store information from the second controller circuitry of the at least one surgical or dental instrument and export the information to a resident or remote data base.

6. The interface device according to claim 3, wherein the first circuitry is further configured to process and store information from the second controller circuitry of the at least one surgical or dental instrument and export the information to a resident or remote data base.

7. The interface device according to claim 2,
    wherein the hardware further includes a display, and
    wherein the first circuitry is further configured to instruct display of information from the second controller circuitry of the at least one surgical or dental instrument and the instructions or data entered by the user on the display.

8. The interface device according to claim 7, wherein the first circuitry is further configured to process and store information from the second controller circuitry of the at least one surgical or dental instrument and export the information to a resident or remote data base.

9. The interface device according to claim 2, wherein the first circuitry is further configured to process and store information from the second controller circuitry of the at least one surgical or dental instrument and export the information to a resident or remote data base.

10. The interface device according to claim 1, wherein the hardware further includes at least one keyboard allowing the user to enter an instruction or data and at least one display configured to display information.

11. The interface device according to claim 1, wherein the first circuitry is connected to the second controller circuitry via a wired connection or a wireless connection.

12. The interface device according to claim 11, wherein, in the case of a wired connection between the first circuitry and the second controller circuitry, the connection occurs via a base or a docket station placed on or fixedly integrated in the power/control unit or the table top equipment.

13. The interface device according to claim 1, wherein the first circuitry and the second controller circuitry of the at least one surgical or dental instrument are connected to each other via a RS-232 serial communication bus.

14. The interface device according to claim 1, wherein the hardware is powered via the second controller circuitry, and wherein the second controller circuitry is powered by the power/control unit or by the table top equipment in which the second controller circuitry is integrated.

15. The interface device according to claim 1, wherein the hardware further includes ordinary batteries or rechargeable batteries, which are recharged via the second controller circuitry integrated in the power/control unit or the table top equipment or which are recharged via a separate charger.

16. The interface device according to claim 1,
wherein the hardware further includes a memory, and
wherein the one or more software modules are loaded to the memory from a personal computer via an integrated connector, via a wireless connection or via a USB stick.

17. The interface device according to claim 1, wherein the hardware is a smartphone.

* * * * *